US00PP19861P2

(12) United States Plant Patent
Klemm

(10) Patent No.: US PP19,861 P2
(45) Date of Patent: Mar. 31, 2009

(54) ***SOLIDAGO* PLANT NAMED 'KLESH06001'**

(50) Latin Name: *Solidago hybrida*
Varietal Denomination: KLESH06001

(75) Inventor: Per Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 12/005,098

(22) Filed: Dec. 20, 2007

(51) Int. Cl.
*A01H 5/00* (2006.01)

(52) U.S. Cl. ..... Plt./483

(58) Field of Classification Search ..... Plt./483
See application file for complete search history.

(56) References Cited

PUBLICATIONS

UPOV–ROM GTITM, Plant Variety Database Feb. 2008, GTI Jouve Retrieval Software, Citation for *Solidago* 'Klesh06001' one page.*

* cited by examiner

*Primary Examiner*—Annette H Para
*Assistant Examiner*—June Hwu
(74) *Attorney, Agent, or Firm*—C. A. Whealy

(57) ABSTRACT

A new and distinct cultivar of *Solidago* plant named 'KLESH06001', characterized by its upright plant habit; freely branching growth habit; early and freely flowering habit; pyramidal spray formation; and inflorescences with light yellow-colored ray florets.

2 Drawing Sheets

Botanical designation: *Solidago hybrida.*
Cultivar denomination: 'KLESH06001'.

BACKGROUND OF THE INVENTION

The present invention relates to a new and distinct cultivar of *Solidago* plant, botanically known as *Solidago hybrida,* and hereinafter referred to by the name 'KLESH06001'.

The new *Solidago* is a product of a planned breeding program conducted by the Inventor in Stuttgart, Germany. The objective of the program is to create and develop new fast-growing *Solidago* cultivars with freely branching habit, flowering habit and attractive inflorescence coloration.

The new *Solidago* originated from a cross-pollination made by the Inventor in October, 2001 of a proprietary selection of *Solidago hybrida* identified as code number J 6, not patented, as the female, or seed, parent with a proprietary selection of *Solidago hybrida* identified as code number J 10, not patented, as the male, or pollen, parent. The new *Solidago* was discovered and selected by the Inventor as a single flowering plant within the progeny of the stated cross-pollination in a controlled environment in Stuttgart, Germany in August, 2002.

Asexual reproduction of the new *Solidago* by terminal cuttings in a controlled environment in Stuttgart, Germany since March, 2003, has shown that the unique features of this new *Solidago* are stable and reproduced true to type in successive generations.

SUMMARY OF THE INVENTION

The cultivar KLESH06001 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'KLESH06001'. These characteristics in combination distinguish 'KLESH06001' as a new and distinct cultivar of *Solidago:*

1. Upright plant habit.
2. Freely branching growth habit.
3. Early and freely flowering habit.
4. Pyramidal spray formation.
5. Inflorescences with light yellow-colored ray florets.

Plants of the new *Solidago* differ from plants of the female parent selection in the following characteristics:

1. Plants of the new *Solidago* are shorter than plants of the female parent selection.
2. Ray florets of plants of the new *Solidago* are lighter yellow in color than ray florets of the female parent selection.

Plants of the new *Solidago* differ from plants of the male parent selection in the following characteristics:

1. Plants of the new *Solidago* are taller than plants of the male parent selection.
2. Sprays of plants of the new *Solidago* are pyramidal in shape whereas sprays of plants of the male parent selection are plume-shaped.

Plants of the new *Solidago* can be compared to plants of the *Solidago* cultivar Tara, not patented. In side-by-side comparisons conducted in Stuttgart, Germany, plants of the new *Solidago* differed from plants of the cultivar Tara in the following characteristics:

1. Plants of the new *Solidago* flowered one week earlier than plants of the cultivar Tara.
2. Sprays of plants of the new *Solidago* were pyramidal in shape whereas sprays of plants of the cultivar Tara were plume-shaped.

BRIEF DESCRIPTION OF THE PHOTOGRAPHS

The accompanying photographs illustrate the overall appearance of the new *Solidago*. This photographs shows the colors as true as it is reasonably possible to obtain in colored reproductions of this type. Colors in the photographs may differ slightly from the color values cited in the detailed botanical description which accurately describe the colors of the new *Solidago*.

The photograph on the first sheet comprises a side perspective view of a typical flowering sprays of 'KLESH06001'.

The photograph on the second sheet is a close-up view of a typical flowering spray of 'KLESH06001'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in Nairobi, Kenya, Germany during the spring in ground beds in a polyethylene-covered greenhouse and under conditions and practices which approximate those generally used in commercial *Solidago* production. During the production of the plants, day temperatures averaged 25° C. and night temperatures averaged 15° C. Measurements and numerical values represent averages for typical flowering plants. Plants were pinched one time and were about four months old when the photographs and description were taken.

Botanical classification: *Solidago hybrida* cultivar KLESH06001.

Parentage:

*Female, or seed, parent.*—Proprietary selection of *Solidago hybrida* identified as code number J 6, not patented.

*Male, or pollen, parent.*—Proprietary selection of *Solidago hybrida* identified as code number J 10, not patented.

Propagation:

*Type.*—Terminal vegetative cuttings.

*Time to initiate roots, summer.*—About 15 days at 18° C.

*Time to initiate roots, winter.*—About 18 days at 20° C.

*Time to produce a rooted cutting.*—About three weeks at 18° C. to 21° C.

*Root description.*—Thick; initially fibrous, with development, fleshy; creamy white in color.

*Rooting habit.*—Freely branching; dense.

Plant description:

*Plant form/growth habit.*—Perennial cut flower typically grown in ground beds; upright plant habit; moderately vigorous growth habit.

*Plant height.*—About 60 cm.

*Plant diameter.*—About 35 cm.

*Lateral branches.*—Plants produce about twelve flowering stems per year. Internode length: About 3 cm. Strength: Moderately strong. Texture: Pubescent. Color: 146D.

*Foliage description.*—Arrangement: Alternate to whorled, simple; sessile. Length: About 8 cm. Width: About 1.3 cm. Shape: Lanceolate. Apex: Acuminate. Base: Acute. Margin: Serrated. Texture, upper and lower surfaces: Pubescent; velvety. Venation pattern: Parallel. Color: Developing foliage, upper surface: 146B. Developing foliage, lower surface: 146C. Fully expanded foliage, upper surface: 137B; venation, 147A. Fully expanded foliage, lower surface: 137C; venation, 148B.

Inflorescence description:

*Appearance.*—Daisy-type inflorescence form with ovate to deltoid-shaped ray florets. Flowering sprays pyramidal in shape; sprays with 25 to 30 branches; about 1000 inflorescences develop per spray. Disc and ray florets develop acropetally on a capitulum. Inflorescences not fragrant. Inflorescences persistent. Inflorescences face upright to outwardly. Uniform and freely flowering habit.

*Flowering response.*—Plants flower from July to October. Early flowering habit; plants begin flowering about ten to twelve weeks after pinching.

*Postproduction longevity.*—Inflorescences maintain good color and substance for about three weeks on the plant and for about ten days as a cut flower.

*Inflorescence bud.*—Height: About 2.5 mm. Diameter: About 1 mm. Shape: Cylindrical. Color: 145A.

*Spray height.*—About 50 cm.

*Spray diameter.*—About 36 cm.

*Inflorescence size.*—Diameter: About 6 mm. Depth (height): About 3 mm. Diameter of disc: About 2 mm. Receptacle height: About 1 mm. Receptacle diameter: About 1 mm.

*Ray florets.*—Number of ray florets per inflorescence/arrangement: About eight arranged in a single whorl. Length: About 3 mm. Width: About 1 mm. Shape: Ovate to deltoid. Apex: Obtuse. Base: Attenuate. Margin: Entire. Texture, upper and lower surfaces: Smooth, glabrous; satiny. Color: When opening, upper and lower surfaces: 9B. Fully opened, upper and lower surfaces: 9B.

*Disc florets.*—Arrangement: Massed at center of receptacle. Number of disc florets per inflorescence: About six. Length: About 3 mm. Diameter, apex: About 1 mm. Diameter, base: About 0.5 mm. Shape: Tubular, salverform, elongated. Apex: Five lobes; lobes acute. Color, immature: 9B. Color, mature: 9B.

*Phyllaries.*—Quantity per inflorescence: About twelve. Length: About 1 mm to 2 mm. Width: About 1 mm. Shape: Oval. Apex: Acute. Base: Obtuse. Texture, upper surface: Pubescent. Texture, lower surface: Smooth, glabrous. Color, upper and lower surfaces: Close to N144C.

*Peduncles.*—Length, terminal peduncle: About 4.5 mm. Length, fourth peduncle: About 4 mm. Length, seventh peduncle: About 9.5 mm. Diameter: About 1 mm. Aspect: About 30° from vertical. Strength: Strong. Texture: Pubescent. Color: 144D.

*Reproductive organs.*—Androecium: Present on disc florets only. Quantity per disc floret: One. Anther shape: Elliptic. Anther length: Less than 1 mm. Anther color: 14A. Pollen amount: Abundant. Pollen color: 14A. Gynoecium: Present on both ray and disc florets. Quantity per floret: One. Pistil length: About 3 mm. Stigma shape: Filamentous. Stigma color: 155A. Style length: About 2 mm. Style color: 155A.

*Seed.*—Seed development has not been observed.

Disease/pest resistance: Plants of the new *Solidago* have been observed to be somewhat resistant to Powdery Mildew. Plants of the new *Solidago* have not been observed to resistant to pests and other pathogens common to *Solidago.*

Temperature tolerance: Plants of the new *Solidago* have been observed to tolerate temperatures ranging from about −10° C. to about 30° C.

It is claimed:

1. A new and distinct *Solidago* plant named 'KLESH06001' as illustrated and described.

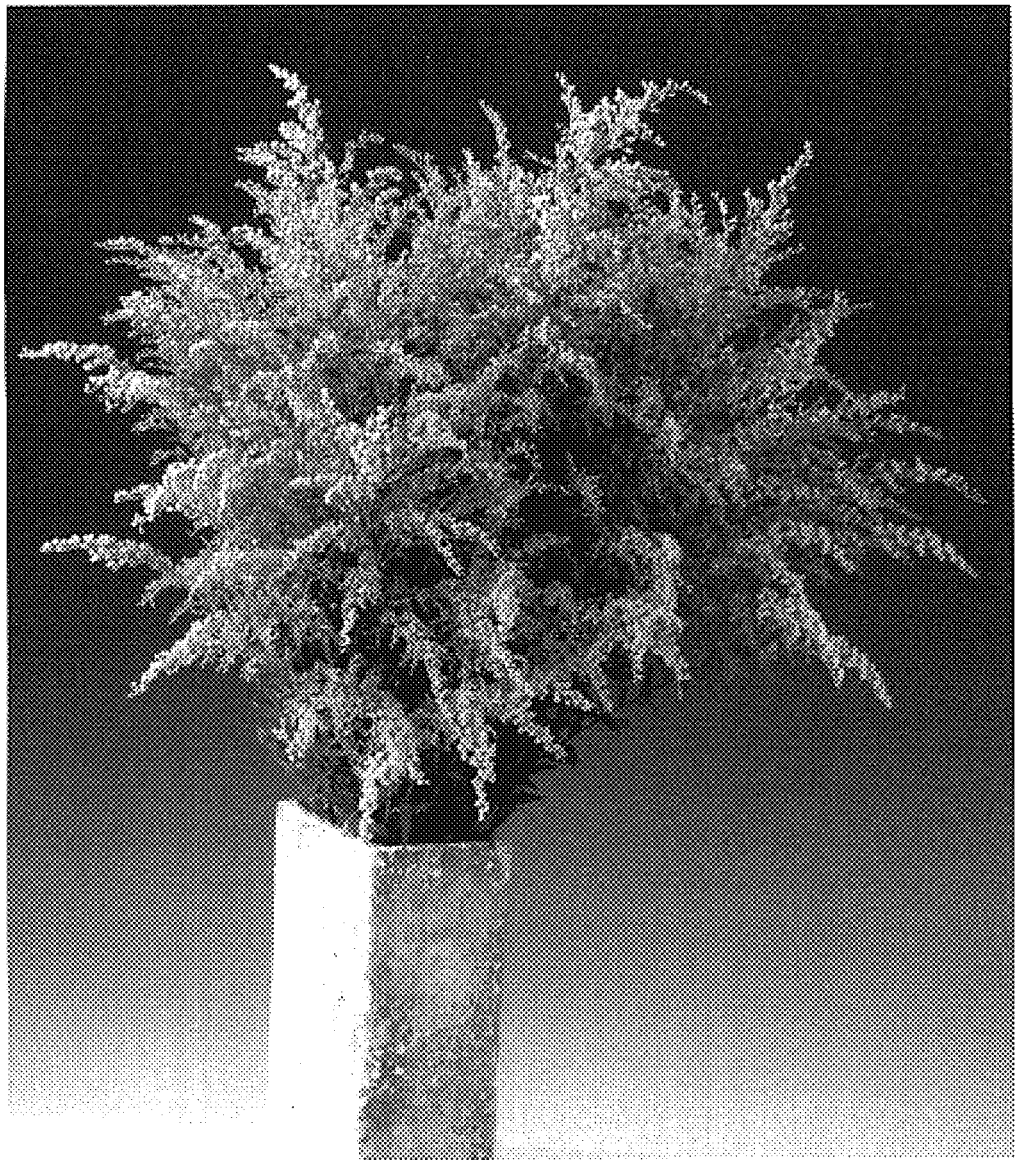

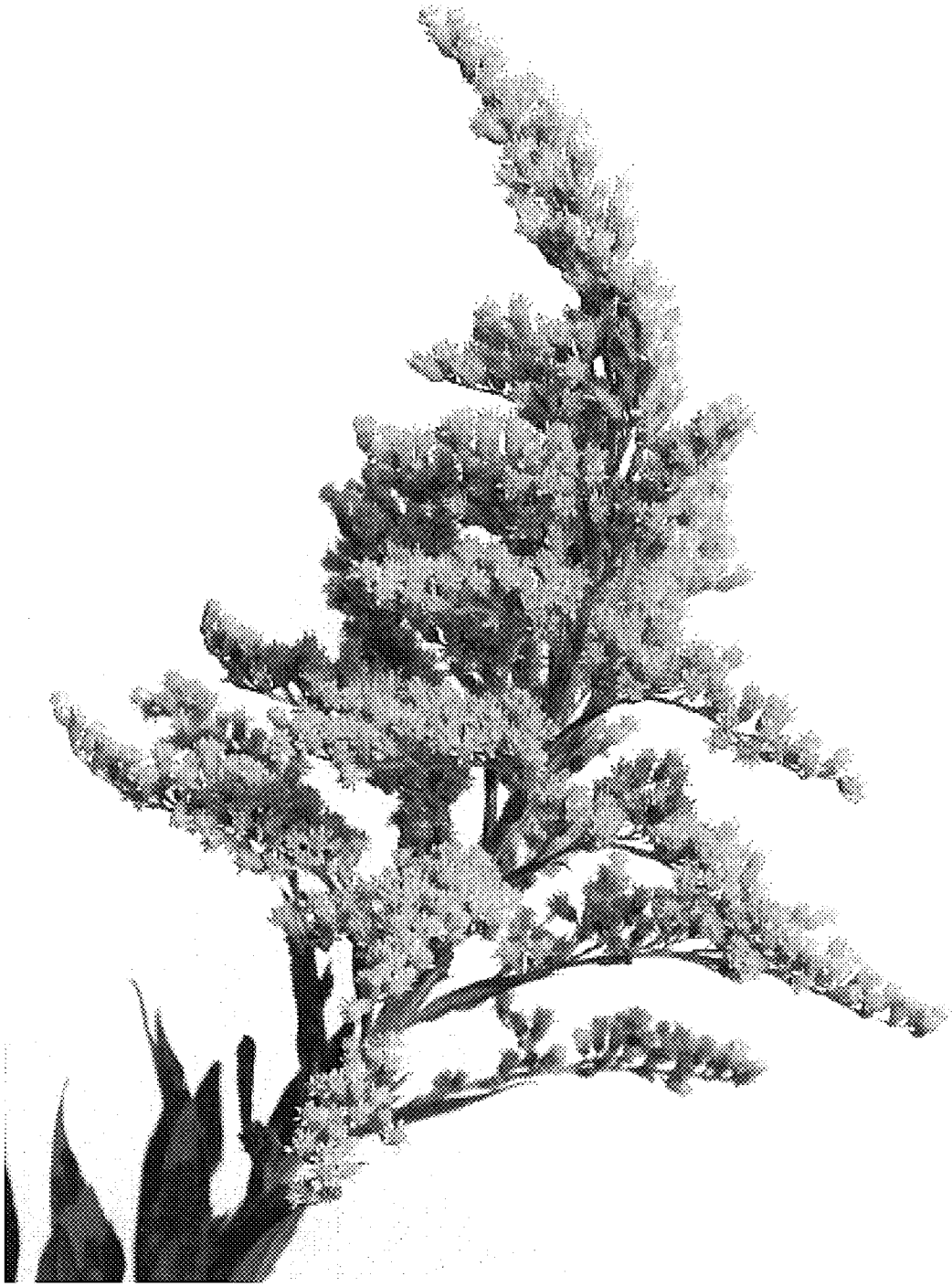

* * * * *